United States Patent
Emerson

(10) Patent No.: US 7,971,730 B2
(45) Date of Patent: *Jul. 5, 2011

(54) COLLECTION TUBES APPARATUS, SYSTEMS AND METHODS

(75) Inventor: Jane Emerson, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 147 days.

This patent is subject to a terminal disclaimer.

(21) Appl. No.: 12/271,610

(22) Filed: Nov. 14, 2008

(65) Prior Publication Data

US 2009/0129973 A1    May 21, 2009

Related U.S. Application Data

(63) Continuation-in-part of application No. 11/933,839, filed on Nov. 1, 2007, now Pat. No. 7,673,758, which is a continuation-in-part of application No. 11/499,436, filed on Aug. 4, 2006, now Pat. No. 7,674,388.

(60) Provisional application No. 60/707,299, filed on Aug. 10, 2005, provisional application No. 61/028,426, filed on Feb. 13, 2008.

(51) Int. Cl.
  *B01D 21/26* (2006.01)
  *B01D 12/00* (2006.01)

(52) U.S. Cl. .......... 210/512.3; 210/511; 210/516; 210/781; 210/782; 210/789; 252/60; 435/2; 522/6

(58) Field of Classification Search .......... None
See application file for complete search history.

(56) References Cited

U.S. PATENT DOCUMENTS

| | | | |
|---|---|---|---|
| 3,647,070 | A | 3/1972 | Adler |
| 3,780,935 | A | 12/1973 | Lukacs |
| 3,920,549 | A | 11/1975 | Gigliello |
| 3,976,579 | A | 8/1976 | Bennett |
| 4,050,451 | A | 9/1977 | Columbus |
| 4,052,320 | A | 10/1977 | Jakubowicz |
| 4,101,422 | A | 7/1978 | Lamont et al. |
| 4,190,535 | A | 2/1980 | Luderer et al. |
| 4,235,725 | A | 11/1980 | Semersky |
| 4,295,974 | A | 10/1981 | Cornell |
| 4,350,593 | A | 9/1982 | Kessler |
| 4,386,003 | A | 5/1983 | Fiehler |
| 4,417,981 | A | 11/1983 | Nugent |
| 4,460,675 | A | 7/1984 | Gruetzmacher |
| 4,569,764 | A | 2/1986 | Satchell |

(Continued)

FOREIGN PATENT DOCUMENTS

EP    0350851    1/1990

(Continued)

*Primary Examiner* — Krishnan S Menon
*Assistant Examiner* — Dirk Bass
(74) *Attorney, Agent, or Firm* — Fish & Associates, PC

(57) ABSTRACT

Methods of producing collection tubes are presented. The methods include providing a separator substance that can rapidly polymerize in a short time to a desired hardness and disposing the separator substance within the lumen of the tube. The separator substance is formulated to have a density between an average density of a serum fraction of whole blood and a cell-containing fraction of whole blood, and to be flowable with whole blood. Upon centrifugation of a tube having blood, the separator substance forms a barrier between the whole blood fractions. The tube and barrier maintain stability of one or more analyte levels, including potassium and glucose, within 10% of their initial values before centrifugation for at least four days.

15 Claims, 3 Drawing Sheets

Blood collection with separator substance.

Blood collection with separator substance of Figure 1A with blood and before centrifugation.

U.S. PATENT DOCUMENTS

| Patent | Type | Date | Inventor |
|---|---|---|---|
| 4,751,001 | A | 6/1988 | Saunders |
| 4,770,779 | A | 9/1988 | Ichikawa et al. |
| 4,816,168 | A | 3/1989 | Carrol et al. |
| 4,818,418 | A | 4/1989 | Saunders |
| 4,844,818 | A | 7/1989 | Smith |
| 4,867,887 | A | 9/1989 | Smith |
| 4,894,315 | A | 1/1990 | Feinberg |
| 4,946,601 | A | 8/1990 | Fiehler |
| 4,994,393 | A | 2/1991 | Pradhan et al. |
| 5,124,434 | A | 6/1992 | O'Brien |
| 5,266,199 | A | 11/1993 | Tsukagoshi |
| 5,304,605 | A | 4/1994 | Murakami et al. |
| 5,336,736 | A | 8/1994 | Nakano |
| 5,354,838 | A | 10/1994 | Murakami et al. |
| 5,454,958 | A | 10/1995 | Fiehler |
| 5,489,386 | A | 2/1996 | Saunders |
| 5,494,590 | A | 2/1996 | Smith |
| 5,505,853 | A | 4/1996 | Satake |
| 5,506,333 | A | 4/1996 | O'Brien et al. |
| 5,510,237 | A | 4/1996 | Isogawa et al. |
| 5,525,227 | A | 6/1996 | Vogler |
| 5,527,843 | A | 6/1996 | Murakmi et al. |
| 5,582,954 | A | 12/1996 | Swatton |
| 5,663,285 | A | 9/1997 | Rounds |
| 5,731,391 | A | 3/1998 | O'Brien et al. |
| 5,776,357 | A | 7/1998 | Okamoto et al. |
| 5,814,220 | A | 9/1998 | Mikami et al. |
| 5,888,824 | A | 3/1999 | Isogawa et al. |
| 5,906,744 | A | 5/1999 | Carroll et al. |
| 5,986,039 | A | 11/1999 | O'Brien et al. |
| 6,072,022 | A | 6/2000 | O'Brien et al. |
| 6,238,578 | B1 | 5/2001 | Fiehler |
| 6,248,844 | B1 | 6/2001 | Gates |
| 6,280,622 | B1 | 8/2001 | Goodrich et al. |
| 6,361,700 | B2 | 3/2002 | Gates |
| 6,979,307 | B2 | 12/2005 | Beretta et al. |
| 6,989,226 | B2 | 1/2006 | Araki |
| 7,090,970 | B2 | 8/2006 | Anraku et al. |
| 2002/0146677 | A1 | 10/2002 | Augello et al. |
| 2006/0160025 | A1 | 7/2006 | Lungu |
| 2006/0212020 | A1 | 9/2006 | Rainen et al. |
| 2007/0003588 | A1 | 1/2007 | Chinn et al. |
| 2007/0005024 | A1 | 1/2007 | Weber et al. |
| 2007/0020629 | A1 | 1/2007 | Ross et al. |
| 2007/0187341 | A1 | 8/2007 | Emerson |
| 2009/0146099 | A1 | 6/2009 | Anraku et al. |

FOREIGN PATENT DOCUMENTS

| | | |
|---|---|---|
| EP | 00705882 | 4/1996 |
| EP | 0766973 | 4/1997 |
| EP | 00928301 | 7/1999 |
| KR | 1020050030337 | 3/2005 |
| KR | 1020050115235 | 12/2005 |
| WO | 9964931 | 12/1999 |
| WO | WO2005011495 | 2/2005 |
| WO | WO2007139018 | 12/2007 |

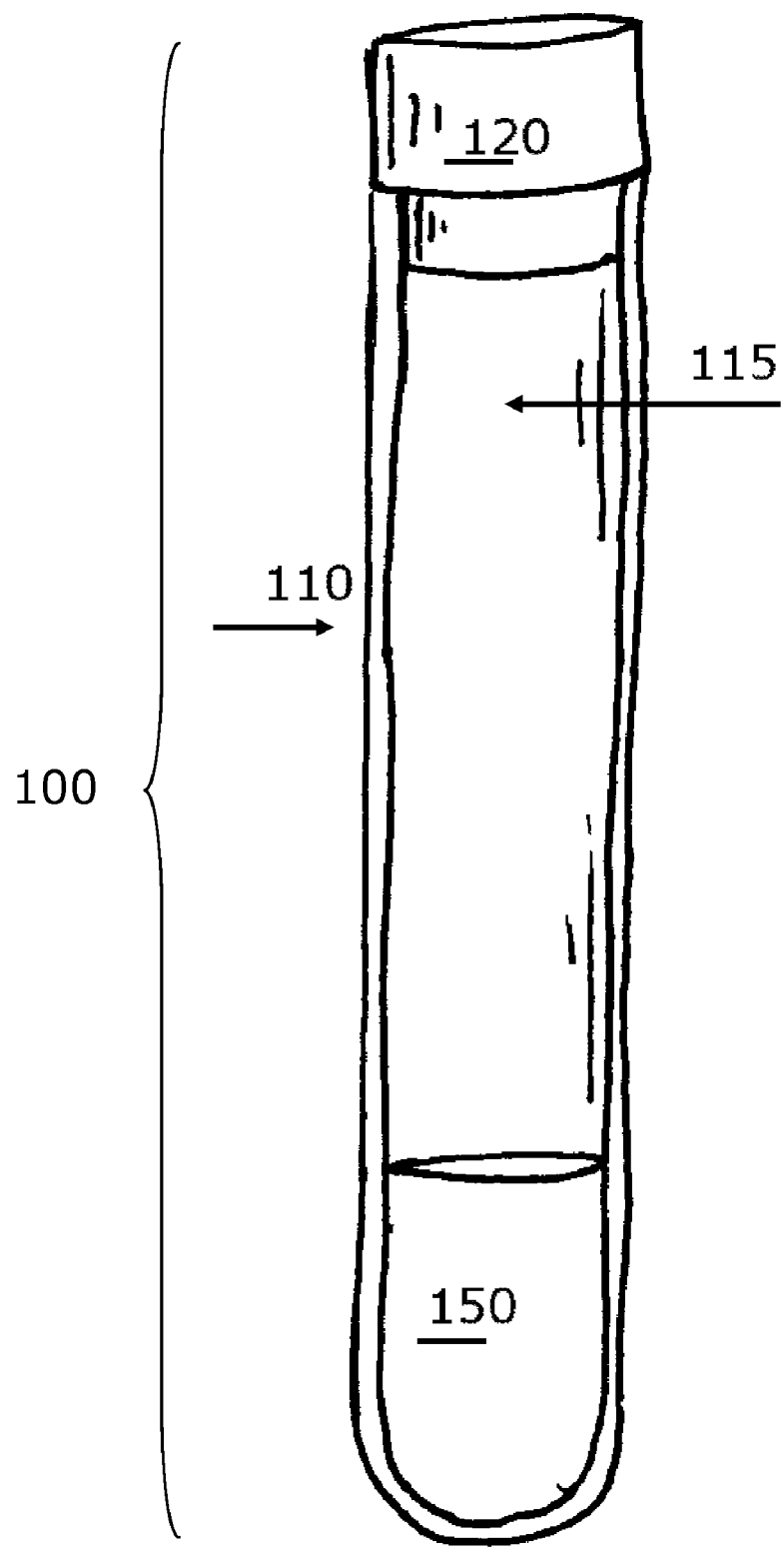
Figure 1A: Blood collection with separator substance.

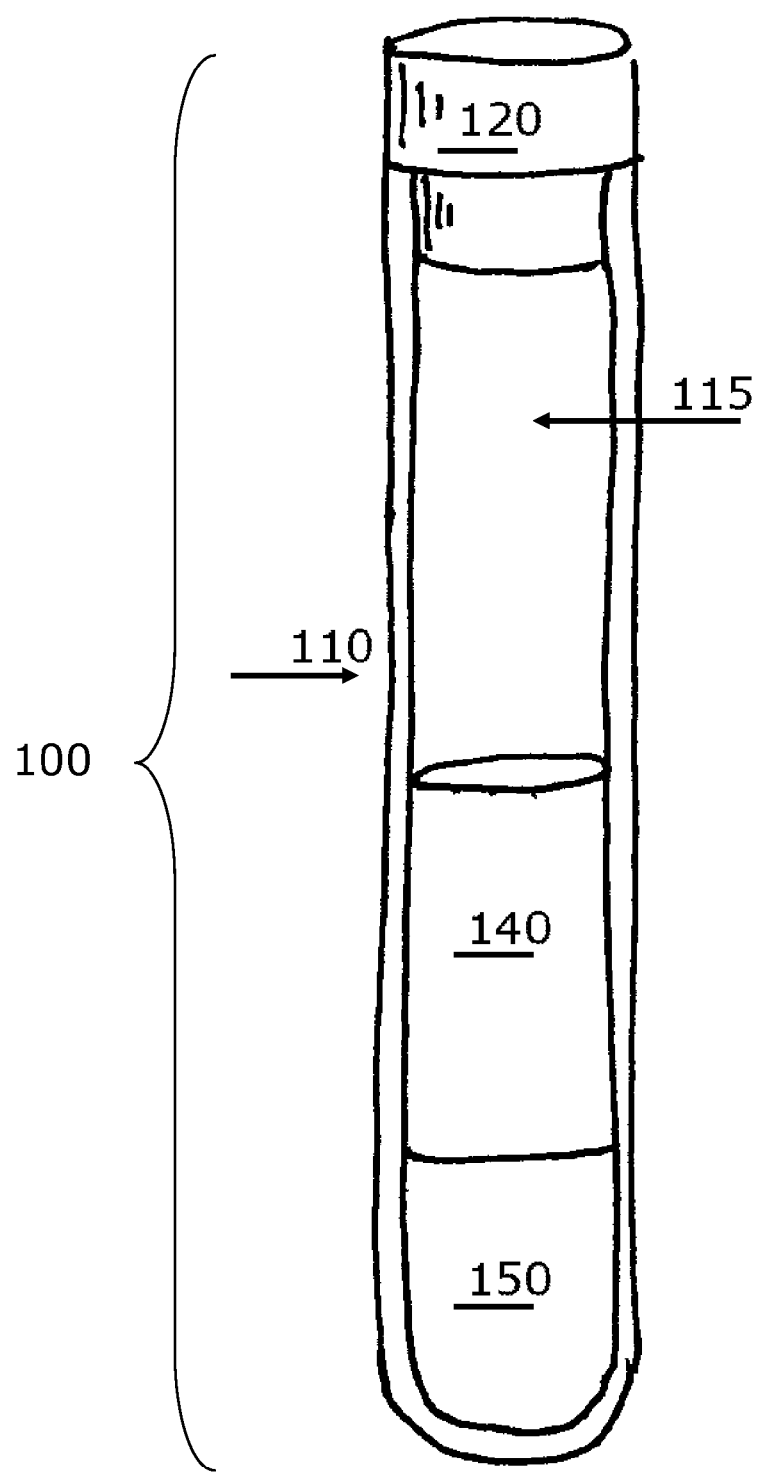
Figure 1B: Blood collection with separator substance of Figure 1A with blood and before centrifugation.

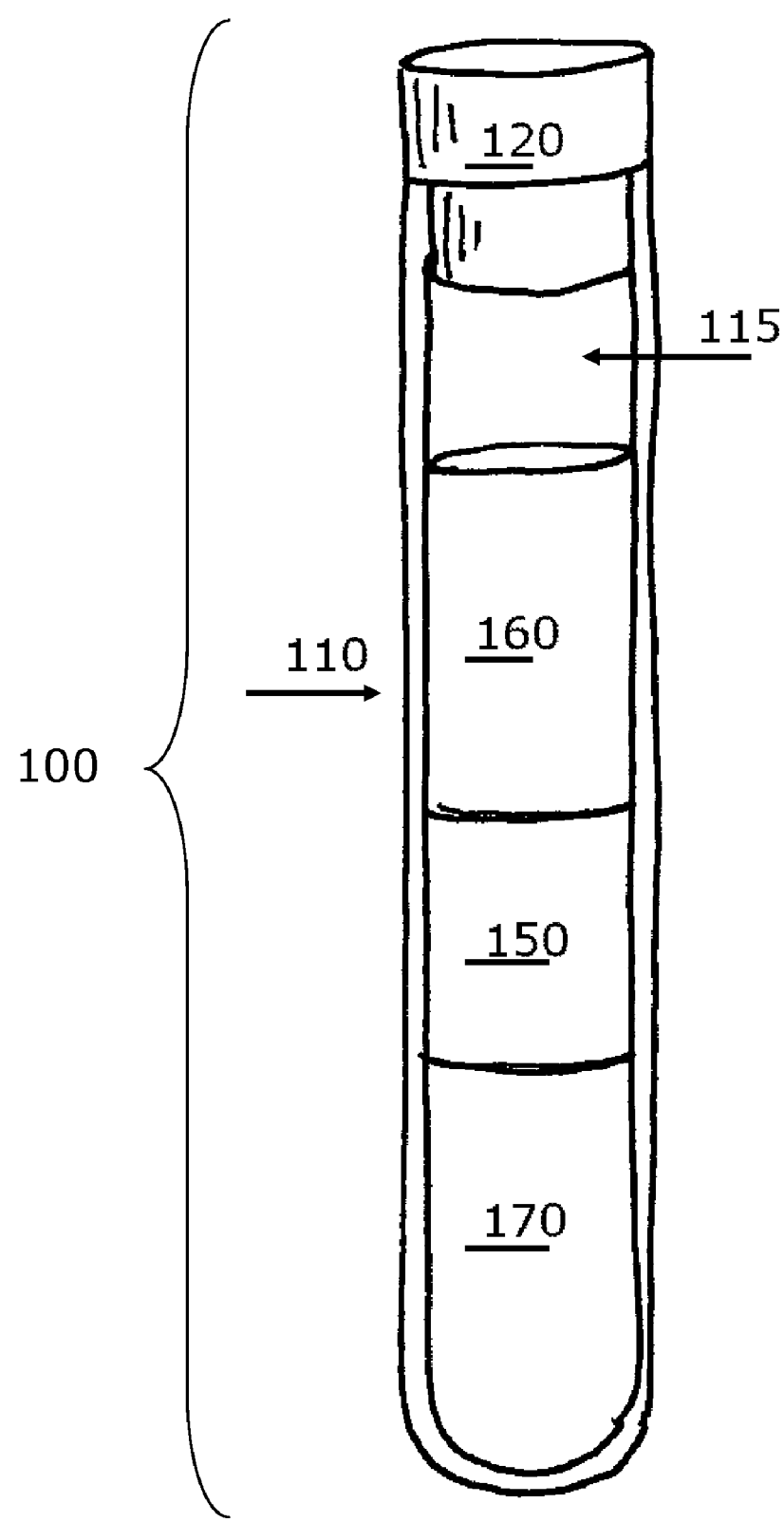
Figure 1C: Blood collection tube of Figure 1B after centrifugation.

COLLECTION TUBES APPARATUS, SYSTEMS AND METHODS

This application is a continuation-in-part of U.S. patent application having Ser. No. 11/939,839 filed on Nov. 1, 2007; which is a continuation-in-part of U.S. patent application having Ser. No. 11/499,436 filed on Aug. 4, 2006; which claims priority to U.S. provisional patent application Ser. No. 60/707,299 filed on Aug. 10, 2005; and this application claims the benefit of priority to U.S. provisional application having Ser. No. 61/028,426 filed on Feb. 13, 2008. These and all other extrinsic references are incorporated herein by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is separation technologies.

BACKGROUND

Analysis of blood samples often requires separation of whole blood into a serum fraction and a cell-containing fraction. It is well known in the art that whole blood separation can be carried out through centrifugation by disposing whole blood into a blood collection tube, placing the tube into a centrifuge, and spinning down the blood.

Unfortunately, once the blood separates, the fractions of the whole blood can remix causing contamination of the fractions through diffusion, agitation, sample extraction, or other undesirable interaction. Ideally, the two fractions should remain isolated to ensure no contamination occurs when accessing the desired fraction. Furthermore, the analytes of the blood should maintain stability after separation over extended periods of time to provide for storage, shipping, or late term analysis.

Any system that isolates the fractions of whole blood must include a separator substance having a suitable density within the tube. Suitable densities are about 1.04 $g/cm^3$ and are between the density of the heavier cell-containing phase and the density of the lighter serum-containing phase. When whole blood is added to the tube and the tube is centrifuged, the separator substance migrates to between the fractions isolating the two fractions from each other. An example collection tube using a gel as a separator substance and that is flowable with whole blood can be found in U.S. Pat. No. 4,946,601 to Fiehler. An example separator substance that is also flowable with whole blood can be found in U.S. Pat. No. 6,248,844 and U.S. Pat. No. 6,361,700 to Gates et. al. In those patents the substance is a polyester curable to a desired viscosity.

Although providing a flowable substance allows for separating the fractions of whole blood, flowable substances have several disadvantages. A flowable substance remains flowable even after centrifugation which results in a risk of contamination of the sample if proper care is not taken to keep the sample suitably still and protected from agitation. For example, it is known to use a thixotropic gel in a blood collection tube where the gel can still flow after centrifugation. Additionally, known substances lack the ability to maintain analytes (e.g., potassium and glucose) at acceptable levels over extended periods of time (e.g., for at least three days).

U.S. Pat. No. 4,818,418 to Saunders discusses the use of a thixotropic gel in blood collection tubes. The problem with thixotropic gels, however, is they do not form a sufficiently permanent separation barrier between the fractions of whole blood. When a sample is extracted from the tube with a pipette, the substance can contaminate or plug the pipette if it touches the substance due to the flowable nature of the substance. If the substance is formulated or configured with a high viscosity to provide a sufficiently solid or permanent barrier to overcome the previous disadvantages, then the substance is no longer suitably flowable with whole blood resulting in prohibitive centrifuge times. Short centrifuge times are critical in life or death situations where a blood analysis result is required quickly.

An alternative approach taken by collection tube manufactures is to provide moveable solid barriers. Examples of suitable solid substances include the intermediate density polymers found in U.S. Pat. No. 3,647,070 where polymer spheres form the barrier layer. U.S. Pat. No. 5,266,199 describes a tube-and-ball valve that controls separation of the serum from the cell-containing phase. However, such physical barriers do not provide a sufficient seal between the fractions and are often either incomplete and tend to leak, or impracticable for other various reasons.

These and other solutions for whole blood separation lack the necessary features to ensure the separated factions of whole blood are effectively protected against contamination due to undesirable sample interactions while supporting short centrifugation times. Furthermore, known separation technologies fail to maintain stability of analytes, especially potassium and glucose, over extended periods of time. Thus, there is still a need for liquid separation technologies in which the separation layer can be hardened and preserve stability of analytes.

SUMMARY OF THE INVENTION

The present invention provides apparatus, systems and methods in which a collection tube includes a separator substance that maintains potassium levels and glucose levels within acceptable thresholds for extended periods of time. In one aspect of the inventive subject matter, potassium levels are stable within 10% of an initial level before centrifugation and glucose levels are stable within 5%. Furthermore, preferred collection tubes are able to keep analytes stable for at least four days, or even up to five days.

Another aspect of the inventive subject matter includes methods of producing collection tubes. A separator substance is disposed within the tube where the substance is formulated aid in keeping analytes stable over extended periods of time. The tube can also be sterilized using gamma radiation or heating the tube to at least 250 degrees Celsius.

Various objects, features, aspects and advantages of the inventive subject matter will become more apparent from the following detailed description of preferred embodiments, along with the accompanying drawings in which like numerals represent like components.

BRIEF DESCRIPTION OF THE DRAWING

FIG. 1A is a side perspective view of a blood collection tube having a polymerizable separator substance that can harden.

FIG. 1B is a side perspective view of the blood collection of tube of FIG. 1A after adding whole blood.

FIG. 1C is a side perspective view of the blood collection tube of FIG. 1B after centrifugation.

DETAILED DESCRIPTION

Collection Tube

In FIG. 1A blood collection tube 100 generally comprises tube 110, plug 120, and separator substance 150, where tube 110 has lumen 115. Tube 110 is preferably manufactured out of a suitably rigid material to support a vacuum within lumen 115. Example materials include hard plastics, glass, or other similar materials. Lumen 115 is of sufficient volume to hold a desirable sample of whole blood or liquid. Typical volumes range from a few ml to 10 ml or greater. Plug 120 fits sufficiently snug into tube 110 to maintain the vacuum within lumen 115. It is contemplated that plug 120 is manufactured to provide a color code or other indication that separator substance 150 is disposed within lumen 115. An example of an acceptable tube that can be used to produce collection tube 100 includes the Vacutainer® specimen collection products developed by Becton, Dickenson and Company (Franklin Lakes, N.J. USA 07417).

The term "tube" is used euphemistically to refer to vessels having a cavity. Although a preferred embodiment includes tube 110, one should appreciate that other vessels having a cavity can also be used while still falling within the scope of the inventive subject matter. For example, it is contemplated that collection tube 100 could be replaced with other vessels that can contain a liquid or optionally support a vacuum. Alternative examples of vessels include flasks, jars, beakers, bottles, blood collection bags, or phials. Vessels beyond mere tubes also have utility when the inventive subject matter is applied to alternative markets beyond blood collection.

In a preferred embodiment, collection tube 100 is produced by disposing separator substance 150 within lumen 115, and introducing a vacuum within lumen 115 in preparation for sale. It is also preferred that no more than about 1 ml, or about 2 grams, of separator substance 150 is disposed into lumen 115 for a typical 10 ml collection tube. It is contemplated that other amounts, more or no more than 1 ml, could also be used to fit a specific use case. For example a smaller version of tube 110 would require less of separator substance 150, while a larger version might require more to make an adequate sealed barrier.

In some embodiments, tube 100 is sterilized before tube 100 is sold. For example, tube 100 can be sterilized using gamma radiation before adding a preferred photopolymer. Another example of sterilization includes heating tube 100 to at least 250 degrees Celsius after adding the preferred photopolymer. It is also contemplated that other methods of sterilization could also be used without departing from the inventive subject matter. Other forms of sterilizations beyond thermal or radiation based sterilization could include chemical sterilization.

An optional vacuum can be introduced by simply decompressing the volume of lumen 115 by using a suitable pump. The term "vacuum" within the context of this document means a partial vacuum having a pressure lower than the pressure external to tube 110.

It is also contemplated that a user could add one or more separator substances to a collection tube after purchase, as opposed to having a separator substance pre-disposed within the tube.

FIG. 1B represents an exemplary embodiment of a blood collection tube after introduction of blood 140, and before centrifugation. Although blood 140 is shown on top of separator substance 150, the two might have characteristics in which they are free to flow or mix.

FIG. 1C represents an exemplary embodiment of a blood collection tube after centrifugation. During centrifugation blood 140 separates into serum fraction 160 and cell-containing fraction 170. When separator substance 150 has a density that is intermediate to that of serum faction 160 and cell-containing fraction 170, it migrates between the two fractions during centrifugation, thereby isolating fractions 160 and 170 from each other. Separator substance 150 can then be rapidly hardened through polymerization when triggered by a suitable energy source.

Separator Substance

Preferably separator substance 150 rapidly hardens during final polymerization to a hardness that is resistant to penetration by a pipette, to decanting, or even to freezing. Preferred substances are solid with respect to a probe, possibly a pipette.

Hardness can be measured using any suitable hardness scale including one of the Shore hardness scales. The Shore 00 hardness scale is used to measure the hardness of soft substances including gels or foams. The Shore A hardness scale is used to measure the hardness of substances having an intermediate hardness including rubbers. The Shore D hardness scale is used to measure the hardness of harder substances including plastics. Although the preceding Shore hardness scales are used for different various substances, the scales all overlap at the low end of their spectrums. Therefore, a value of 10 on the Shore D scale is harder than a value of 10 on the Shore A scale which in turn is harder than a value of 10 on the Shore 00 scale. Separator substance 150 is preferably formulated to harden to at least 1 on the Shore 00 hardness scale. More preferred embodiments of separator substance 150 harden further to at least 10 on the Shore A hardness scale. In yet other embodiments separator substance 150 harden even further to at least 10 on the Shore D hardness scale.

Within the context of this document, the term "rapidly hardens" means to harden to at least 1 on the Shore 00 hardness scale within at least 10 minutes. One of the aspects of the inventive subject matter is appreciating that a shorter time to harden can be advantageous over a longer timer. Having separator substance that hardens within a few minutes, for example, could be important for a hospital to analyze a sample in a critical life or death situation. In preferred embodiments, the time to harden is no more than 5 minutes, more preferably no more than 1 minute, and most preferably no more than 10 seconds.

The hardened barrier of preferred separator substances adheres to the walls of lumen 115 substantially sealing the cell-containing fraction and protecting the fractions from contamination due to diffusion, agitation, sample extraction, or other undesirable interaction. In preferred embodiments the final thickness of the barrier is no more than 5 mm.

Separator substance 150 is preferably a biocompatible organic polymer. Among other things, biocompatibility means that the separator substance 150 does not interfere with or alter characteristics of the substances being tested. In the case of blood, for example, the separator substance 150 should not interfere with pH, enzyme activities, or with concentrations of pigments, proteins, gases, or any other analytes.

In yet other embodiments, it is contemplated that the substance could include a component that intentionally reacts with the sample being separated. For example, the separator substance could include a coagulant, blood thinner, or other substance that interacts with whole blood.

In blood separation tubes, the separator substance 150 should have a density of between about 1.01-1.09 $g/cm^3$, and most preferably about 1.04 g/cm³. Unless the context dictates otherwise, all ranges herein are to be interpreted as being inclusive of their endpoints.

An acceptable separator substance can include a polyester backbone similar to those described in U.S. Pat. Nos. 6,361,700 and 6,248,844, both of which are incorporated by reference herein. Polymerization is preferably carried out to achieve the desired density of between about 1.04-1.06 g/cm³. However, and in contrast to the methods and compositions provided in the '700 and '844 patent, polymerization is not run to completion but stopped using a polymerization terminator (e.g., using radical quenchers, catalyst complexing agent, etc.) in a minimum amount effective to stop further polymerization.

As the sample contacts the incompletely cured polymer (separator substance 150), it is contemplated that the polymerization terminator is diluted to a concentration that allows the polymerization to be re-initiated. Prior to re-initiation, blood 140 is separated in the container by centrifugation, which will leave cell-containing fraction 170 in the bottom portion of tube 110 and serum fraction 160 in the upper portion of tube 110, wherein both fractions are separated by the incompletely cured polymer (separator substance 150). Re-initiation of polymerization may be assisted by irradiating the polymer with UV light or other suitable energy source. Thus, it should be appreciated that the polymeric is additionally cured after the separation is completed and the so separated serum can then be accessed without contamination of a pipette, decanted, or even frozen. Moreover, it should be recognized that the final cured barrier layer is substantially permanent (i.e., stable over several days, or even weeks).

While it is generally acceptable that collection tube 100 include a polyester polymer as separator substance 150, it should be noted that the exact nature of the polymeric material is not limiting to the inventive subject matter, and that numerous alternative polymers are also suitable. Indeed all known polymers suitable for whole blood separation are deemed appropriate for use herein, including silicon oil, polyamides, olefinic polymers, polyacrylates polyesters and copolymers thereof, polysilanes, and polyisoprenes. To achieve a desired initial density (typically between about 1.03 and 1.05), it is contemplated that the density may be adjusted by virtue of molecular composition, as well as by inclusion of appropriate filler material (e.g., silica, latex, or other inert material). For example, suitable polymeric materials are described in U.S. Pat. Nos. 3,647,070, 3,920,557, or 3,780,935, or in EP 0 928 301 or 0 705 882, which are incorporated by reference herein. Furthermore, it is contemplated that the serum separators may include additional materials and/or reagents to achieve a desired bio-reactive purpose. For example, the separators presented herein may include EDTA, heparin, citrate, dextrose, etc. It should be noted that the term "serum" is used herein to also include plasma, and other substantially cell free fluids derived from whole blood.

Depending on the particular material, it is contemplated that the mode and/or mechanism of polymerization to the separator polymer may vary considerably, and all know manners of polymerization are deemed suitable for use herein. For example, contemplated polymerizations include various radical or cationic polymerizations (e.g., using photolabile compounds, radical starters, etc.), condensation polymerizations, esterifications, amide formation, etc. Thus, reactive groups will especially include acid groups (and most preferably mono- and dicarboxylic groups), conjugated diene groups, aromatic vinyl groups, and alkyl(meth)acrylate. Such exemplary reactive groups and reaction conditions are described, for example, in U.S. Pat. No. 6,989,226, which is incorporated by reference herein. It should furthermore be appreciated that the reactive groups can be coupled to the terminus of a polymer as end groups as described in WO 99/64931, which is incorporated by reference herein, or that the reactive groups may be provided as pendant groups (e.g., as described in U.S. Pat. No. 5,336,736, incorporated by reference herein).

It is generally preferred that polymerization is fully supported by reactive groups on pre-polymer, but additional reagents may also be suitable, including radical starters, including those described in U.S. Pat. Nos. 5,582,954, 4,894,315, and 4,460,675, which are incorporated by reference herein. Additionally contemplated separator substances also include those that provide a crosslinking group to the polymer such that the polymer has reactive groups that react with a bifunctional crosslinker (e.g., ethylenically unsaturated compounds) to thereby form crosslinked polymers. Yet additional contemplated separator substances also include those having promoters that accelerate polymerization.

An acceptable example of separator substance 150 includes a substance known as "M1L1A1" co-developed by the University of Maryland and University of California Irvine. M1L1A1 is a polymeric separator substance comprising the following: (M1) a monomer Trimethylolpropane propoxylate triacrylate from Sigma-Aldrich Cat. No. 407577, (L1) CYTEC Aliphatic Urethane Acrylate EBECRYL 230 from Cytec Industries, Inc., and (A1) Additol BDK, 2,2-Dimethoxy-1,2-diphenyl-ethan-1-one also from Cytec Industries, Inc. Additionally, M1L1A1 has desirable properties for use with whole blood including an adjustable density by adding fumed silica, it is flowable in whole blood when centrifuged, thixotropic, a hardness greater than 10 on the Shore A hardness scale after polymerization, hardens in no more than 10 seconds under exposure to UV light, biocompatible with whole blood, and forms a hardened seal impermeable to the cell-containing fraction of whole blood and that is resistant to penetration of a pipette. M1L1A1 hardens under a UV light source that radiates light in the wavelengths from 10 nm to 450 nm. A preferred UV light source radiates in the range 250 nm to 400 nm. All suitable energy sources are contemplated for triggering polymerization. It is contemplated that an existing centrifuge having a UV source can be used to polymerize the separator substance, or a centrifuge can incorporate a suitable energy source capable of triggering polymerization.

Preferably, the temperature of the collection tube contents changes by no more than 10 degrees Celsius during polymerization; more preferably by no more than 5 degrees Celsius. Short exposure times ensures the sample will maintain appropriate pigment levels, gas levels, temperatures, protein levels, or other characteristics associated with whole blood.

Preferred separator substances, including photopolymers such as M1L1A1, have additional desirable properties beyond those discussed above. For example, desirable substances are substantially transparent. After centrifugation, the transparency of separation barrier allows an analyst or technician to visually determine the completeness of separation. The technician can easily observe if red blood cells, or other matter, are trapped within the substance. Additionally, it is contemplated that the substances can be formulated to have a desirable color (i.e., can include dyes) to aid in identifying tubes or to clearly indicate the location of the separation barriers between two or more factions of blood. It is specifically contemplated that separator substances can have a color that corresponds to a coded cap of a collection tube (e.g., green, gold, yellow, etc. . . . ).

Analyte Stability

Preferred separator substances preserve the stability of one or more analytes of the serum or cell-containing fraction of a blood sample for extended periods of time. Maintaining stability of analytes allows long term storage, shipping of samples, or delayed analysis. For example, blood samples can be collected in remote locations and then sent to a lab located days, possibly weeks away.

Preferred studies comparing and contrasting collection tubes include collecting statistics from at least ten collection tubes, measuring analyte levels periodically, and averaging the results for each analyte period. Such studies utilize nominal conditions including room temperature (e.g., about 20 degrees Celsius), lack of external agitation, or other external influences.

TABLE 1

| Analytes | BD Vacutainer with PST ™ gel and Lithium Heparin | | | | BD Vacutainer with PST gel, Lithium Heparin, and M1L1A1 | | | |
| --- | --- | --- | --- | --- | --- | --- | --- | --- |
| | Init. | 1 Day | 5 Day | Freeze - Thaw | Init. | 1 Day | 5 Day | Freeze - Thaw |
| Sodium | 142 | 139 | 140 | 143 | 140 | 140 | 142 | 143 |
| Potassium | 3.7 | 3.7 | 4.1 | 4.5 | 3.6 | 3.6 | 3.7 | 3.8 |
| Chlorides | 106 | 104 | 105 | 108 | 106 | 105 | 107 | 108 |
| $CO_2$ | 29 | 27 | 26 | 22 | 27 | 25 | 25 | 22 |
| Glucose | 102 | 100 | 93 | 91 | 104 | 105 | 102 | 106 |
| Urea Nitrogen | 16 | 15 | 16 | 16 | 17 | 16 | 16 | 16 |
| Creatinine | 0.6 | 0.8 | 0.8 | 0.6 | 0.7 | 0.8 | 0.8 | 0.5 |
| Calcium | 9.4 | 9.3 | 9.5 | 9.7 | 9.2 | 9.4 | 9.5 | 9.6 |
| Total Protein | 6.8 | 6.8 | 6.4 | 7.0 | 6.8 | 7.0 | 6.7 | 7.0 |
| Albumin | 4 | 4 | 4 | 4 | 4 | 4.1 | 4.1 | 4 |
| Alk. Phos. | 37 | 39 | 36 | 38 | 36 | 38 | 39 | 37 |
| AST | 17 | 15 | 19 | 26 | 17 | 17 | 18 | 16 |
| ALT | 15 | 16 | 19 | 16 | 16 | 17 | 17 | 13 |
| Total Bilirubin | 0.6 | 0.7 | 0.6 | 0.5 | 0.5 | 0.6 | 0.6 | 0.4 |

In a preferred embodiment, a value of an analyte changes by less than 10% over an extended period of time after centrifugation relative to a value before centrifugation. In more preferred embodiments, analytes change by less than 5%, and yet more preferably by less than 3%, and even yet more preferably by less than 1%.

As used herein "extended period of time" is considered to be at least three days and more preferably at least four days. In more preferred embodiments a separator substance maintains stability of an analyte for five or more days. Unless a contrary intent is apparent from the context, all ranges recited herein are inclusive of their endpoints, and open-ended ranges should be interpreted to include only commercially practical values.

Preferred embodiments utilizing the contemplated separator substance also maintain analyte stability across extreme environmental conditions. For example, in a preferred embodiment, analytes stability is maintained across a freezing-thawing event.

Analytes of particular interest include potassium or glucose. Preferred tubes maintain potassium levels within 10% for at least four days after centrifugation. Additionally, the substances preferably maintain glucose levels within 5% for at least four days after centrifugation.

Several studies were conducted by the Applicant to compare and contrast a commercially available collection tube (i.e., BD Vacutainer with PST™ gel and Lithium Heparin) with a similar collection tube having M1L1A1 added as a separator substance. The results of one the studies conducted by the Applicant are presented in Table 1 below. The study included taking measurements of initial levels of analytes immediately after centrifugation (see columns "Init.") and comparing the measurements taken after storage, (see columns "1 Day" and "5 Day"). Additionally, measurements were obtained after a freezing-thawing event (see columns "Freeze-Thaw"). One should note that as used herein an "initial level" of an analyte should be considered to be the level of an analyte just after centrifugation as measured within a reasonable time frame to conduct an analysis.

As can be seen in Table 1, a collection tube utilizing a preferred separate substance (e.g., M1L1A1) maintains analytes at stable levels over extended periods of time and across extreme conditions. For example, potassium levels are maintained within 3% of an initial level after centrifugation for at least five days. Additionally, glucose levels are maintained within 2% of an initial level after centrifugation for at least five days. It should also be noted that the levels of analytes are also maintained across a freeze-thaw event. The commercially available tube lacks such features with respect to potassium and glucose. One should also note that the commercially available tube was unable to maintain levels of AST across the freeze-thaw event while the tube having a preferred substance was able to maintain AST levels.

Alternative Embodiments

Although the preferred embodiment of the inventive subject matter primarily focuses on blood collection tubes, one should recognize that the systems, apparatus, and methods presented herein can be applied to alternative markets beyond blood collection tubes. Similar techniques to those disclosed herein can also be employed to separate nearly any fluid having more than one constituent phase. For example, a separator substance can be provided to separate fluids including urine, water samples, oil, wine, or other multi-phase fluids. For fluids having more than two phases, it is contemplated that a collection tube can contain more than one separator substances which are used to separate at least three phases of the fluid.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A blood collection tube, comprising;

A tube having a lumen;

A separator substance disposed within the lumen, and adapted to separate a blood sample into at least a serum fraction and a cell-containing fraction upon centrifugation, the separator substance comprising a curable compound having sufficient reactive groups permitting polymerization of the compound to a crosslinked composition within 10 minutes to a cured hardness of at least 1 on the Shore 00 harness scale when curing of the substance is triggered by a suitable energy source; and Wherein after centrifugation and formation of the crosslinked composition in the tube maintains for at least four days a potassium level of the blood within 10% of an initial potassium level, and maintains a glucose level of the blood within 5% of an initial glucose level.

2. The tube of claim 1, wherein the substance is substantially transparent.

3. The tube of claim 1, wherein the substance comprises a color.

4. The tube of claim 3, wherein the color approximately corresponds to a color associated with a cap for the tube.

5. The tube of claim 1, wherein after centrifugation the substance is solid with respect to a probe.

6. The tube of claim 1, wherein the substance is curable to a hardness of at least 1 on the Shore A hardness scale when exposed to a suitable energy source.

7. The tube of claim 1, wherein after centrifugation the tube maintains the potassium level of the blood within 10% and maintains the glucose level of the blood within 5% across a freezing-thawing event.

8. The tube of claim 1, wherein after centrifugation the substance lacks visibly trapped cells.

9. The tube of claim 1, wherein after centrifugation the tube maintains the potassium level within 10% and the glucose level within 5% for at least five days.

10. A method of producing a blood collection tube, comprising;

Providing a tube having a lumen;

Providing a separator substance comprising a curable compound having sufficient reactive groups permitting polymerization of the compound to a crosslinked composition within 10 minutes to a cured hardness of at least 1 on the Shore 00 hardness scale when curing of the substance is triggered by a suitable energy source, which, after centrifugation and formation of the crosslinked composition, maintains a potassium level of the blood within 10% of an initial potassium level, and maintains a glucose level of the blood within 5% of an initial glucose level.

11. The method of claim 10, further comprising sterilizing the tube.

12. The method of claim 11, wherein the step of sterilization includes exposing the tube to gamma radiation.

13. The method of claim 11, wherein the step of sterilization includes heating the tube to at least 250 degrees Celsius.

14. The method of claim 10, further comprising curing the substance to a harness of at least 1 on the Shore A scale.

15. The method of claim 10, further comprising introducing a vacuum into the lumen of the tube.

* * * * *